(12) United States Patent
Itoh

(10) Patent No.: US 10,343,796 B2
(45) Date of Patent: Jul. 9, 2019

(54) CAP-CLOSING APPARATUS, CAP-CLOSING UNIT AND CAP-CLOSING METHOD

(71) Applicant: AOI SEIKI CO., LTD., Kumamoto-shi, Kumamoto-ken (JP)

(72) Inventor: Teruaki Itoh, Kumamoto (JP)

(73) Assignee: AOI SEIKI CO., LTD., Kumamoto (JP)

( * ) Notice: Subject to any disclaimer, the term of this patent is extended or adjusted under 35 U.S.C. 154(b) by 489 days.

(21) Appl. No.: 15/068,678

(22) Filed: Mar. 14, 2016

(65) Prior Publication Data
US 2016/0272348 A1 Sep. 22, 2016

(30) Foreign Application Priority Data
Mar. 18, 2015 (JP) .................. 2015-054872

(51) Int. Cl.
| | |
|---|---|
| B65B 7/28 | (2006.01) |
| G01N 35/04 | (2006.01) |
| B01L 3/00 | (2006.01) |
| B67B 3/26 | (2006.01) |

(52) U.S. Cl.
CPC ........... *B65B 7/2835* (2013.01); *G01N 35/04* (2013.01); *B01L 3/50825* (2013.01); *B67B 3/261* (2013.01); *G01N 2035/0405* (2013.01)

(58) Field of Classification Search
CPC ........... G02N 2035/0405; B67B 3/261; B01L 3/50825; B65B 7/2835
USPC .......................................... 53/490, 317, 471
See application file for complete search history.

(56) References Cited

U.S. PATENT DOCUMENTS

| | | | |
|---|---|---|---|
| 4,696,144 A * | 9/1987 | Bankuty ............... | B67B 3/2053 53/314 |
| 5,493,849 A | 2/1996 | Itoh | |
| 2009/0056285 A1* | 3/2009 | Kramer ................. | G01N 35/04 53/492 |
| 2010/0126116 A1 | 5/2010 | Buchhauser et al. | |
| 2010/0307108 A1* | 12/2010 | Sink ..................... | B65B 7/2835 53/285 |

(Continued)

FOREIGN PATENT DOCUMENTS

| | | |
|---|---|---|
| CN | 201040708 | 3/2008 |
| CN | 202575915 | 12/2012 |

(Continued)

OTHER PUBLICATIONS

Extended European Search Report issued in App. No. 16159233.2 dated Jul. 20, 2016.

(Continued)

*Primary Examiner* — Robert F Long
*Assistant Examiner* — Xavier A Madison
(74) *Attorney, Agent, or Firm* — Nixon & Vanderhye P.C.

(57) ABSTRACT

According to an embodiment, a cap-closing apparatus includes, a holding mechanism section configured to be capable of holding a cap which is attached to an opening of a specimen container that is formed to be capable of containing a specimen, a moving mechanism section configured to move the cap, a rotating mechanism section configured to rotate the cap, a torque detector configured to detect a torque at a time of rotation, and a controller configured to control an amount of rotation of the rotating mechanism section, based on the torque detected by the torque detector.

6 Claims, 6 Drawing Sheets

(56) References Cited

U.S. PATENT DOCUMENTS

| | | | |
|---|---|---|---|
| 2014/0174028 A1* | 6/2014 | Yamagata | G01N 35/00 53/287 |
| 2014/0193848 A1 | 7/2014 | Kaufman | |
| 2015/0175398 A1* | 6/2015 | Christensen | B67B 3/20 53/490 |

FOREIGN PATENT DOCUMENTS

| | | |
|---|---|---|
| CN | 101734598 | 1/2014 |
| CN | 103635808 | 3/2014 |
| CN | 203715217 | 7/2014 |
| JP | S63-114995 | 7/1988 |
| JP | 6-239389 | 8/1994 |
| JP | H07-156944 | 6/1995 |
| JP | H07-156994 | 6/1995 |
| JP | 2003-526105 | 9/2003 |
| JP | 2015-525720 | 9/2015 |
| TW | 200823145 | 6/2008 |
| WO | WO 01/67066 | 9/2001 |
| WO | WO 2013/002216 | 1/2013 |
| WO | WO 2013-002216 | 1/2013 |
| WO | WO 2014/023683 | 2/2014 |

OTHER PUBLICATIONS

Korean Office Action issued in Appl. No. 10-2016-0032190 dated Jul. 7, 2017 (w/ translation).

Canadian Office Action issued in Applcation No. 2,923,534 dated Sep. 6, 2017.

Taiwanese Office Action issued in App. No. 105107772 dated Nov. 28, 2016 (w/ translation).

Chinese Office Action issued in Appln. No. 201610154491.4 dated Dec. 1, 2017 (w/ translation).

A First Office Action dated Sep. 18, 2018, in a corresponding Japanese Patent Application No. 2015-054872 (3 pages), with English translation (3 pages).

* cited by examiner

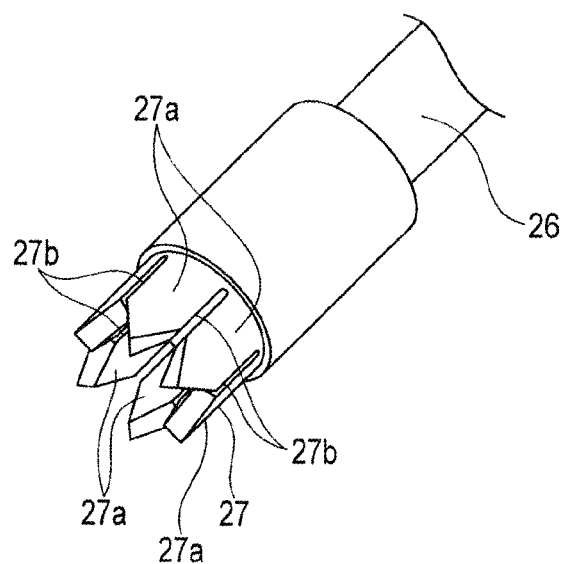
F I G. 7

US 10,343,796 B2

CAP-CLOSING APPARATUS, CAP-CLOSING UNIT AND CAP-CLOSING METHOD

CROSS-REFERENCE TO RELATED APPLICATION

This application is based upon and claims the benefit of priority from the prior Japanese Patent Application No. 2015-054872, filed Mar. 18, 2015 the entire contents of them are incorporated herein by reference.

FIELD

The present invention relates to a cap-closing apparatus, a cap-closing unit and a cap-closing method.

BACKGROUND

In a specimen process of, for example, an examination or analysis of a specimen such as blood or serum, a specimen container is held in a holder in an upright state and conveyed, and various processes are performed by various detection devices disposed on a convey path of the holder. In such a specimen process, a cap is attached for closing the opening of the specimen container. For example, in the state in which the specimen container is held, a cap formed of a material with high flexibility, such as rubber, is pushed in the opening of the specimen container, and thereby the cap is attached (As described in Jpn. Pat. Appln. KOKAI Publication No. 6-239389). In addition, a screw-type cap has been proposed in order to enhance sealing performance. The sealing performance of the screw-type cap deteriorates if the fastening of the screw-type cap is loose. Thus, there is a demand for a technique for exactly attaching the cap.

SUMMARY

According to an embodiment, a cap-closing apparatus comprises, a holding mechanism section configured to be capable of holding a cap which is attached to an opening of a specimen container that is formed to be capable of containing a specimen, a moving mechanism section configured to move the cap, a rotating mechanism section configured to rotate the cap, a torque detector configured to detect a torque at a time of rotation, and a controller configured to control an amount of rotation of the rotating mechanism section, based on the torque detected by the torque detector.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE DRAWINGS

FIG. 7 is a perspective view illustrating the structure of an engaging section of a holding shaft of the cap-closing section.

DETAILED DESCRIPTION

Figure 1:
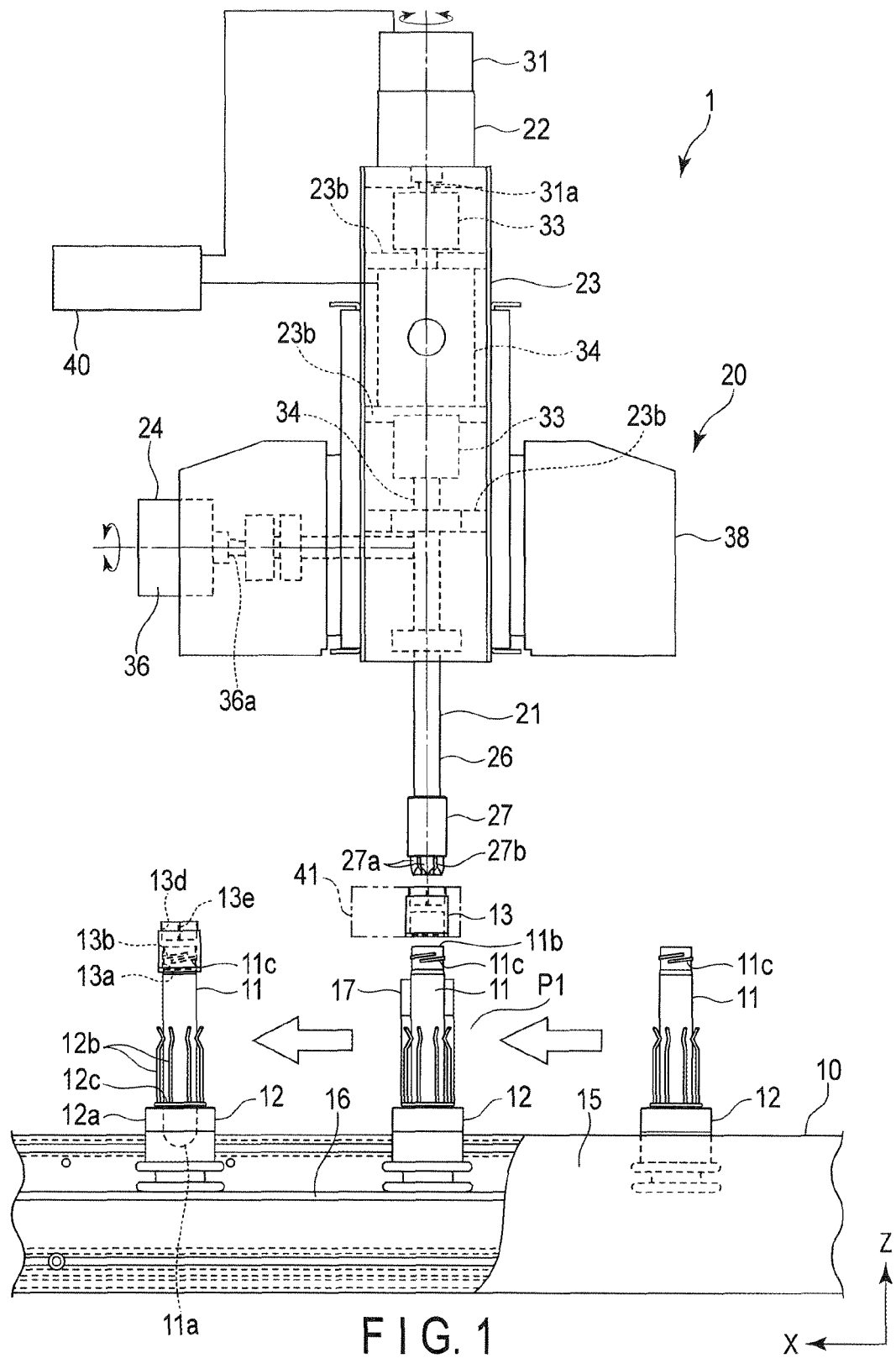
FIG. 1 is a front view of a cap-closing apparatus according to an embodiment of the present invention.
Figure 2:
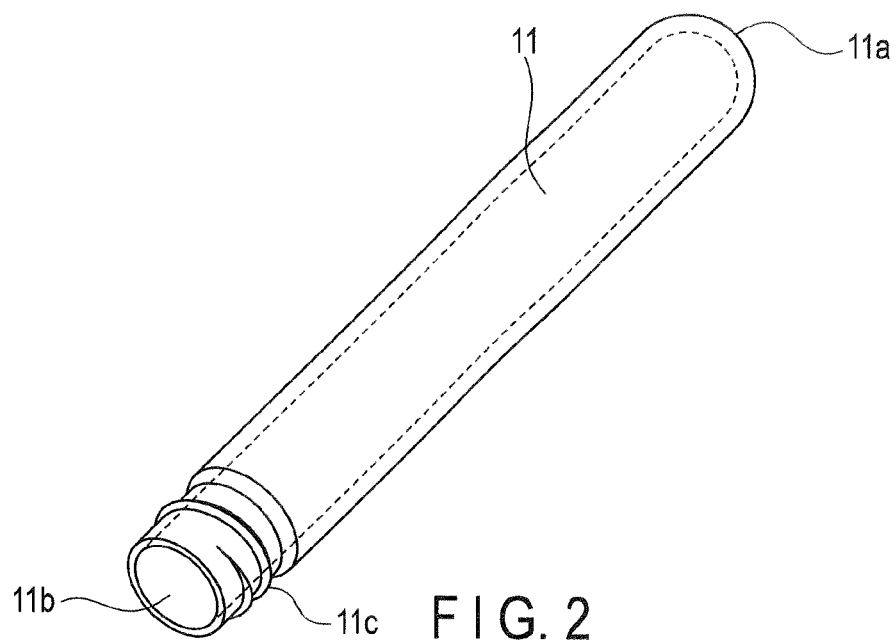
FIG. 2 is a perspective view illustrating the structure of a specimen container according to the embodiment.
Figure 3:
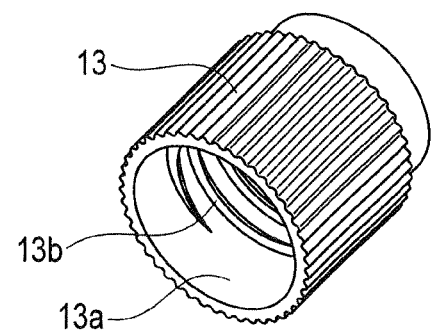
FIG. 3 is a perspective view illustrating the structure of a cap according to the embodiment.
Figure 4:
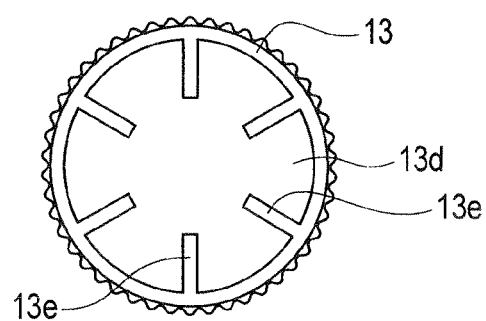
FIG. 4 is a top view illustrating the structure of the cap.
Figure 5:
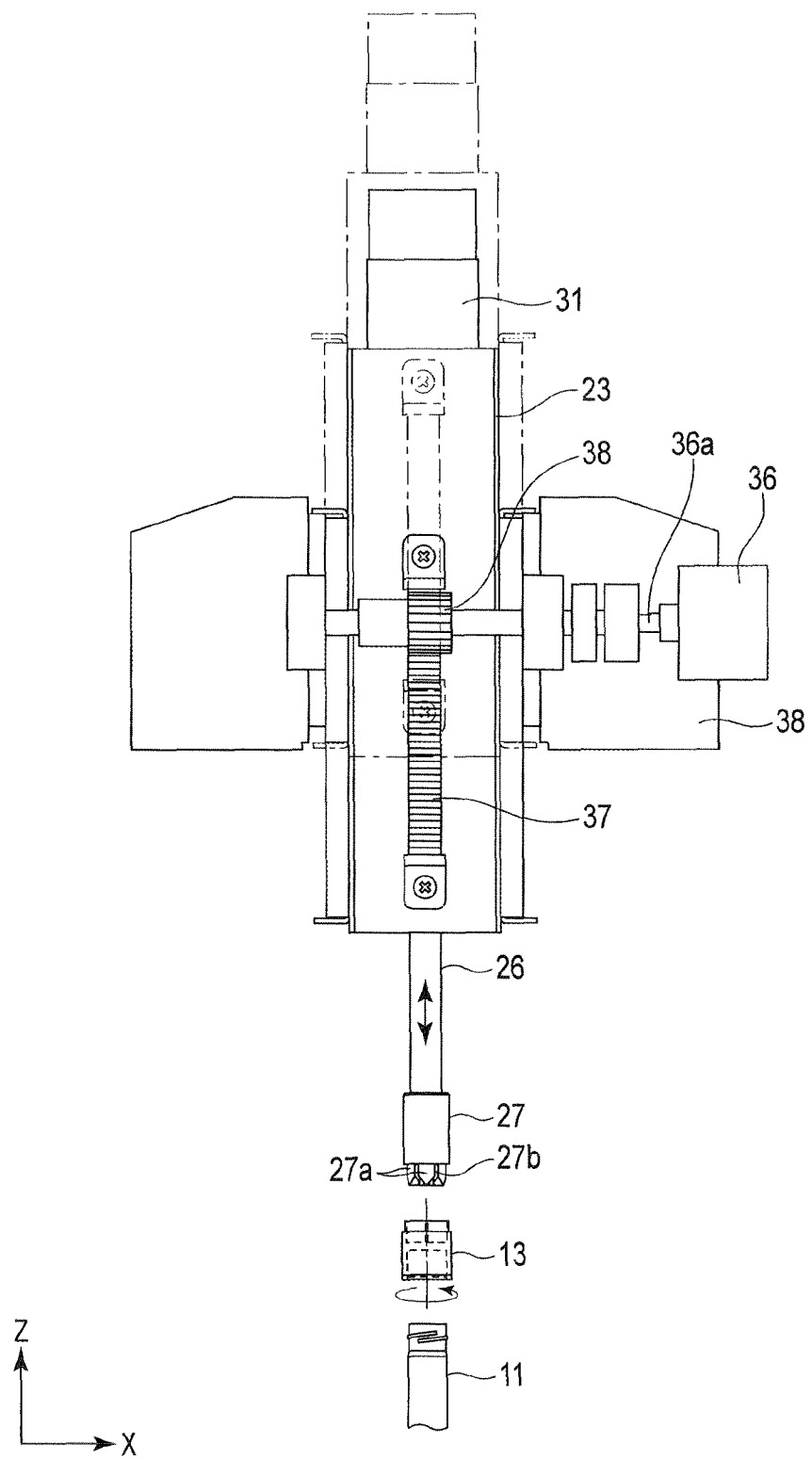
FIG. 5 is a rear view of a cap-closing section according to the embodiment.
Figure 6:
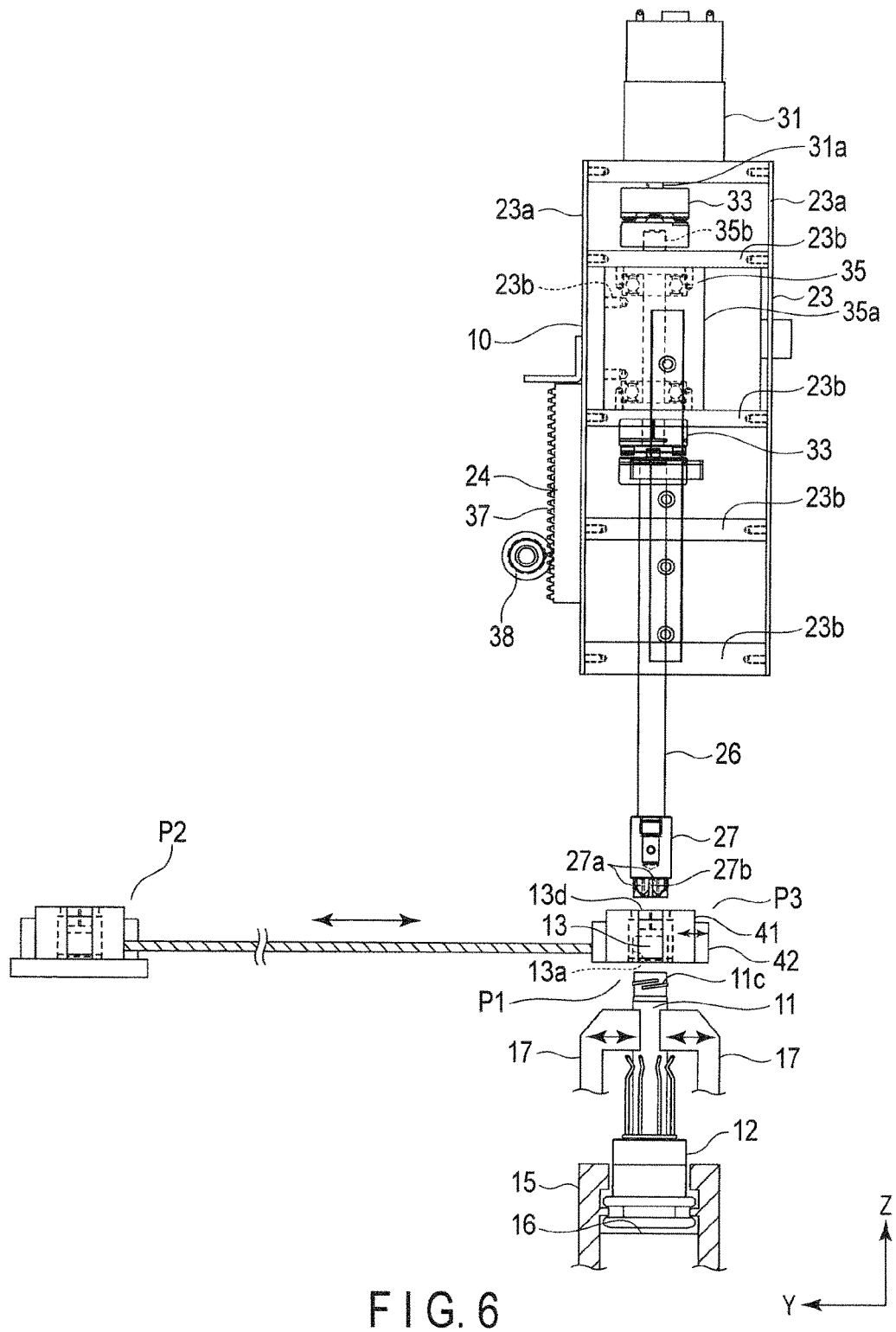
FIG. 6 is an explanatory view illustrating the structure of the cap-closing section.
Figure 8:
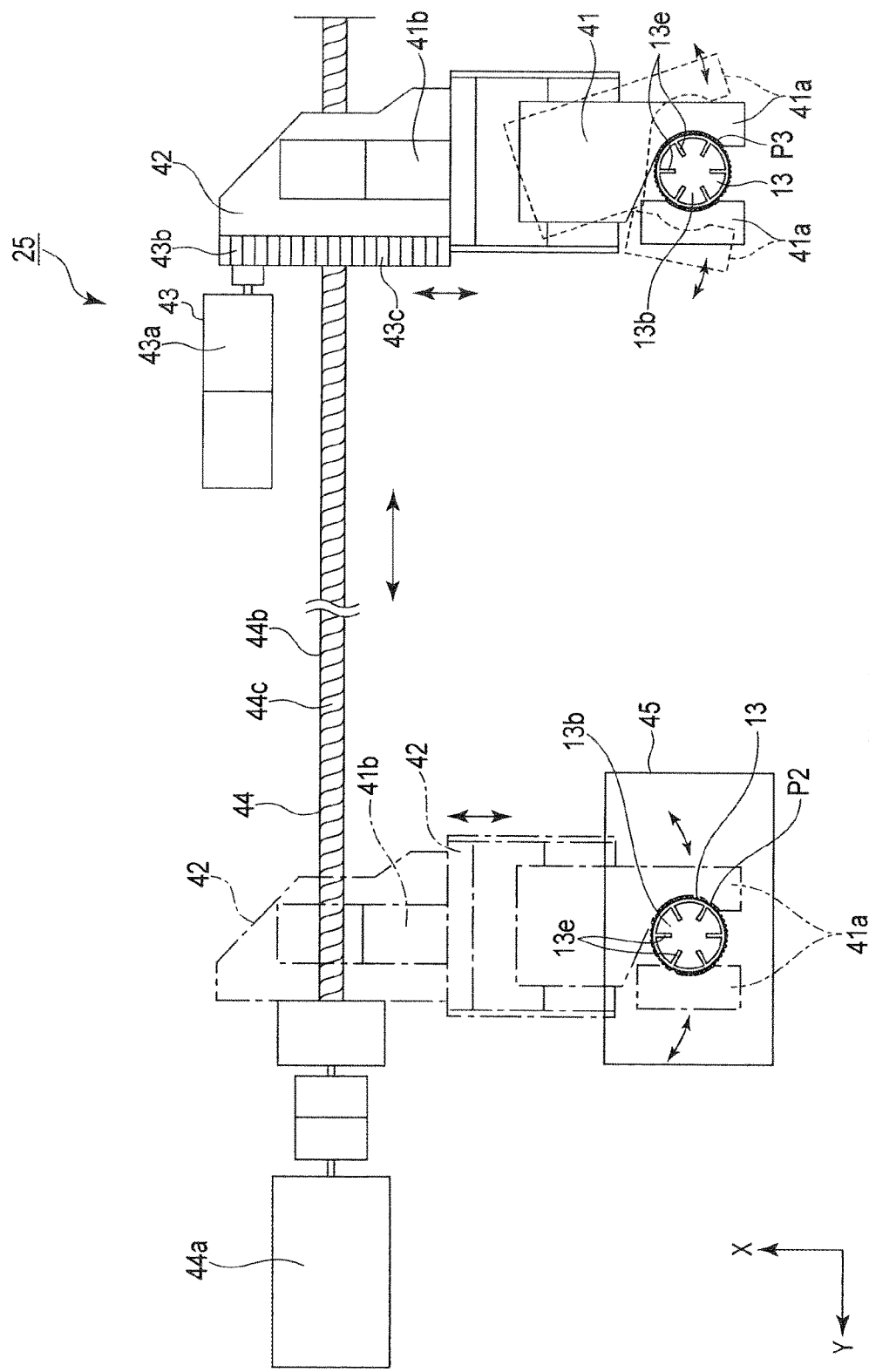
FIG. 8 is a plan view illustrating the structure of a feeding mechanism of the cap-closing apparatus according to the embodiment.

A cap-closing apparatus 1 according to an embodiment of the present invention will be described hereinafter with reference to FIG. 1 to FIG. 8. Incidentally, in the drawings, structures are illustrated with enlargement, reduction or omission, as needed. In the drawings, arrows X, Y and Z indicate three directions which are perpendicular to each other. FIG. 1 is a front view of a cap-closing apparatus 1 according to a first embodiment. FIG. 2 is a perspective view illustrating the structure of a specimen container 11. FIG. 3 is a perspective view illustrating the structure of a cap 13. FIG. 4 is a top view illustrating the structure of the cap 13. FIG. 5 is a rear view of a cap-closing section. FIG. 6 is an explanatory view illustrating, by a partial cross section, the structure of the cap-closing section. FIG. 7 is a perspective view illustrating the structure of a distal end portion of a holding shaft 26.

The cap-closing apparatus 1 shown in FIG. 1 includes a convey unit 10 which conveys a specimen container 11 along a predetermined path; a cap-closing section 20 which attaches a cap to an upper-face opening of the specimen container 11; and a control device 40 which is a controller that controls operations of respective parts. The cap-closing apparatus 1 is one of preprocessing apparatuses, which successively performs a cap-closing process for a plurality of specimen containers 11 prior to various examinations.

The specimen container 11 shown in FIG. 1 and FIG. 2 is a tube-type specimen container which is formed of a transparent glass or resin material, such as a test tube or a blood collection tube. The specimen container 11 is formed in a bottomed cylindrical shape having therein a space which can contain a specimen. The specimen container 11 includes a curved bottom portion 11a, and has a circular opening 11b at an upper part thereof. The upper part of the specimen container 11 constitutes a male screw portion 11c with a helical thread groove formed on an outer peripheral surface thereof. A bar code including, for example, identification information, is attached to an outer peripheral side surface of the specimen container 11. The specimen container 11 is a test tube with a thickness of φ13 mm, φ16 mm, etc., and a length of 75 mm, 100 mm, etc.

As illustrated in FIG. 1, FIG. 3 and FIG. 4, the cap 13, which is attached to the specimen container 11, formed of, for example, a synthetic resin material by resin forming. The cap 13 includes, on one end side in the axial direction, an insertion portion 13a which is a cylindrical space in which the upper part of the specimen container 11 is inserted. A female screw portion 13b having a helical thread, which is engaged with the male screw portion 11c, is formed on an inner peripheral surface of the insertion portion 13a. A plurality of grooves for antislipping are formed on the outer periphery of the cap 13.

A holding hole 13d, which is a cylindrical space for insertion of a holding shaft 26 (to be described later) of the cap-closing section 20, is formed on the other end side in the axis direction of the cap 13. Six longitudinal plates 13e, which serve as engaging recess-and-projection portions each having a pair of major surfaces extending in the radial direction and axial direction, are erectingly provided in the circumferential direction in the holding hole 13e. The longitudinal plate 13e is configured to have a slightly less width dimension than the width dimension of a slit 27b of the engaging section 27, so that the longitudinal plate 13e is engaged in the slit 27b when the holding shaft 26 is inserted in the holding hole 13d.

The convey unit 10 shown in FIG. 1 is a belt conveyor-type convey mechanism, and includes a holder 12 which holds the specimen container 11 in an upright state; a pair of guide rails which are disposed with a fixed width along a predetermined convey path; a convey belt 16 which is formed of, for example, rubber, and is disposed along the convey path between the guide rails 15; a plurality of convey rollers provided on the back side of the convey belt 16; and a convey motor serving as a driving source which rotates and drives the convey rollers.

The holder 12 is configured to be capable of holding the specimen container 11. The holder 12 includes a holding body 12a with an insertion hole that opens at an upper part thereof, a plurality of holding pins 12b which are erectingly provided upward from an upper end of the outer periphery of the holding body 12a, and a holding ring 12c surrounding the periphery of the plural holding pins 12b.

The bottom portion 11a of the specimen container 11 is inserted in the insertion hole and supported by the holding body 12a, and the outer periphery of the side portion of the specimen container 11 is held by the plural holding pins 12b. At this time, the holding ring 12c urges the holding pins 12b radially inward, and thereby the outer peripheral surface of the specimen container 11 is clamped by the plural holding pins 12b.

By the feeding movement of the convey belt 16 which is caused by the rotation of the convey rollers, the convey unit 10 conveys, along a predetermined convey path, the holders 12 which are placed on the convey belt 16 between the paired guide rails 15. On the convey belt 16 of the convey unit 10, the holders 12 are fed by the movement of the convey belt 16 from the upstream side to downstream side. The convey unit 10 stops the holder 12 at a cap-closing position P1 located along the convey path, where a cap-closing process is performed. A pair of holding portions 17, between which the holder 12 is clamped and disposed, are provided at the cap-closing position P1 of the guide rails 15. The holding portions 17 are opened/closed by the control of the control device 40, thereby holding and releasing the side portion of the specimen container 11 which stops at the cap-closing position P1.

As illustrated in FIG. 1, FIG. 5 and FIG. 6, the cap-closing section 20 includes a holding mechanism section 21 which holds the cap 13; a rotating mechanism section 22 which rotates the holding mechanism section 21; a support frame 23 which is a support section that supports the holding mechanism section 21 and rotating mechanism section 22; a moving mechanism section 24 which reciprocally moves the support frame 23 in a Z axis direction; and a feeding mechanism section 25 which feeds the cap 3 to a predetermined standby position P3. In FIG. 1, depiction of the feeding mechanism section 25 is omitted, and only a portion thereof is indicated by a broken line.

The holding mechanism section 21 includes a holding shaft 26 having an engaging section at a distal end thereof. The holding shaft 26 can rise and fall at a predetermined position along the convey path, and is disposed in the up-and-down direction. One end side of the holding shaft 26 is disposed under the support frame 23, and the other end side of the holding shaft 26 is accommodated within the support frame 23 and connected to a rotating motor 31 via a torque sensor 35. An engaging section 27 is formed at a distal end of the holding shaft 26.

The engaging section 27 includes six insertion portions 27a about a rotational axis thereof. A slit 27b is formed between neighboring ones of the insertion portions 27a, the slit 27b being configured such that the longitudinal plate 13e can enter the slit 27b. A distal end side of each insertion portion 27a has a tapered shape with a gradually decreasing thickness. When the engaging section 27 is inserted in the holding hole 13d of the cap 13, the longitudinal plates 13e of the cap 13 enter the slits 27b. Thereby, the engaging section 27 of the holding shaft 26 is engaged with the cap 13, and the cap 13 is held by the holding shaft 26. At this time, since the insertion portion 27a has the tapered shape with a gradually decreasing thickness, the insertion portion 27a is so guided as to be inserted in a space between the longitudinal plates 13e when the holding shaft 26 moves downward and rotates, even if the longitudinal plates 13e of the cap 13 and the slit 27b are misaligned.

In this engaged state, a rotational movement of the holding shaft 26 by the rotating motor 31 is transmitted to the cap 13 via the longitudinal plates 13e and slits 27b.

The proximal end side of the holding shaft 26 is connected to an output shaft 31a of the rotating motor 31 via the torque sensor 35.

The rotating mechanism section 22 includes the rotating motor 31 including the output shaft 31a which is coupled to the holding shaft 26. The output shaft 31a of the rotating motor 31 extends within the support frame 23, and is connected to the holding shaft 26 via the torque sensor 35. The rotating motor 31 rotates and drives the holding shaft 26 at a predetermined timing by the control of the control device 40.

The support frame 23 is a casing which forms an accommodation space for accommodating the torque sensor 35. The support frame 23 includes a plurality of frame members 23a which constitute an outer shell having a rectangular shape in outer appearance, and a plurality of support plates 23b which are laid in the width direction within the accommodation space.

A shaft 34 composed of the output shaft 31a of the motor 31, sensor shaft 35b and holding shaft 26, which are coupled by couplers 33, extends continuously within the support frame 23. In addition, the torque sensor 35, which is a torque detector, is fixed to the support plates 23b within the support frame 23. The rotating motor 31 is fixed to the upper surface of the support frame 23.

The torque sensor 35 is a non-contact magnetostriction-type torque sensor. The torque sensor 35 includes a housing 35a, the sensor shaft 35b connected to the holding shaft 26, and an excitation/detection coil, a magnetic shield, an amplifier board and a connector which are disposed around the sensor shaft 35b.

The housing 35a is fixed to the support frame 23 by a fastening member such as a screw. The sensor shaft 35b extends within the housing 35a. A magnetic material with excellent magnetostriction characteristics is used for the sensor shaft 35b. One end side of the sensor shaft 35b is connected to the holding shaft 26 via the coupler 33, and the other end side of the sensor shaft 35b is connected to an output shaft 36a of a moving motor 36 via the coupler 33. The excitation/detection coil converts a variation in magnetic characteristic, which corresponds to a torque amount, to an electric signal. The amplifier board supplies an excitation voltage to an excitation coil, and amplifies an electric signal (voltage) from an excitation coil.

In the torque sensor 35, if a torque is applied to the sensor shaft 35$b$, a tensile stress or a compressive stress acts selectively on a pair of magnetostrictive members to which anisotropy is imparted, and thereby magnetic permeability varies due to an inverse magnetostrictive effect. The variation in magnetic permeability is subjected to direct-current conversion and differential amplification by the detection coil and amplifier board, thereby obtaining a voltage output which is proportional to the torque.

The moving mechanism section 24 includes the moving motor 36, a rack gear 37 which is attached to the back surface of the support frame 23, and a pinion gear 38 which is provided on the output shaft 36$a$ of the moving motor 36 and is configured to be engageable with the rack gear 37.

The rack gear 37 is an elongated plate-shaped member, and a plurality of teeth, which are arranged in the Z direction, are formed on the rack gear 37.

The moving motor 36 is a rotary motor which can rotate in the forward and backward directions, and is supported in a lateral direction on a rear part of a bracket for disposing the cap-closing section 20 in a predetermined position. The output shaft 36$a$ of the moving motor 36 extends in parallel to the convey direction. A shaft body 38$a$ of the pinion gear 38 is connected and fixed to the distal end of the output shaft 36$a$ of the moving motor 36 by the coupler 33.

The pinion gear 38 is configured to include a plurality of teeth which are juxtaposed on the outer peripheral surface in the circumferential direction, and is disposed on the rear part of the support frame 23 such that the pinion gear 38 is meshed with the rack gear 37 that is provided on the support frame 23.

By the pinion gear 38 being rotated by the driving of the moving motor 36, the rack gear 37 is relatively raised or lowered, and the support frame 23 is raised and lowered. By this raising/lowering operation, the support shaft 26 can reciprocally move, above the specimen container 11, in directions toward and away from the upper opening of the specimen container 11.

The feeding mechanism section 25 includes an opening/closing arm 41 configured to be capable of holding and releasing the cap 13; an arm bracket 42 which supports the opening/closing arm 41; an arm moving mechanism section 43 which reciprocally moves the arm bracket 42 in the X direction; and a screw-type moving mechanism section 44 which reciprocally moves the arm bracket 42, together with the arm moving mechanism section 43, in the Y direction.

The opening/closing arm 41 includes a pair of opening/closing portions 41$a$ which grasp the cap 13, and a motor 41$b$ which rotates the opening/closing portions 41$a$ about a predetermined axis.

By the motor 41$b$ being rotated and driven in forward and backward directions, the opening/closing arm 41 rotates such that the opening/closing portions 41$a$ move toward and away from each other, thereby holding the cap 13 or releasing the cap 13.

The arm moving mechanism section 43 includes a rotary motor 43$a$, a pinion gear 43$b$ which is connected to an output shaft of the rotary motor 43$a$ and is rotated and driven, and a rack gear 43$c$ which is disposed to be meshed with the pinion gear 43$b$ and is fixed to the arm bracket 42.

In the arm moving mechanism section 43, the pinion gear 43$b$ rotates about the Y axis by the forward/backward rotation of the rotary motor 43$a$, and the rack gear 43$c$ with teeth juxtaposed in the X direction moves reciprocally in the X direction. In accordance with this, the arm bracket 42, to which the rack gear 43$c$ is fixed, reciprocally moves in the X direction in the state in which the arm bracket 42 supports the opening/closing arm 41.

The screw-type moving mechanism section 44 includes a rotary motor 44$a$, and a screw 44$b$ which is connected to an output shaft of the rotary motor 44$a$. A helical recess-and-projection portion 44$c$ is formed on the outer peripheral surface of the screw 44$b$. The arm bracket 42 is engaged with, and supported by, the helical recess-and-projection portion 44$c$. The screw 44$b$ has a function of converting a rotational movement about the axis of the screw 44$b$ to a linear movement in the axis direction.

If the rotary motor 44$a$ is rotated and driven in the forward and backward directions, the screw 44$b$, which is disposed along the Y axis, rotates, and thereby the arm bracket 42, which is engaged with the helical recess-and-projection portion 44$c$ on the outer surface of the screw 44$b$, reciprocally moves along the Y axis.

The control unit 40 includes a storage unit which stores various pieces of information; a data processing unit which executes data processing, such as arithmetic operations and determination, based on identification information, etc.; and a driving unit which drives the respective motors. The control device 40 is electrically connected to the torque sensor 35. In addition, the control device 40 is connected to the motors 31 and 36 of the cap-closing section 20, and controls the operation of the rotational mechanism section 22, based on the torque detected by the torque sensor 35. Furthermore, the control device 40 is connected to the various motors 41$b$, 43$a$ and 44$a$ of the feeding mechanism section 25, and repeats the feeding operation of the cap 13 at a predetermined timing.

The control device 40 controls the convey unit 10, and repeats the feeding/stopping operation of the convey belt 16 at a predetermined timing. Besides, the control device 40 includes a function of rotating the holding mechanism section 21 which holds the cap 13, by controlling the operation of the rotating motor 31. The control device 40 includes a function of raising/lowering the holding mechanism section 21 together with the support frame 23, by controlling the operation of the moving motor 36.

Next, a cap-closing method using the cap-closing section 20 according to the embodiment is described.

The control device 40 controls the convey motor of the convey unit 10, thereby moving the holder 12 from the upstream side to downstream side along a predetermined convey path. If the control device 40 detects that the holder 12 has reached the cap-closing position P1, for example, by a sensor or the like provided on a lateral side of the convey path, the control device 40 stops the conveyance. The control device 40 repeats the feed movement and stop of the belt, for example, at a predetermined timing.

The control device 40 controls the feeding mechanism section 25, thereby feeding the cap 13. For example, the opening/closing operation of the opening/closing arm 41 and the reciprocal movement of the arm bracket 42 in the X direction and Y direction are repeated at a predetermined timing, and a series of processes of grasping, movement, releasing and movement is repeated at a predetermined timing. Thereby, the caps 13 are successively fed from the feed table 45 to the standby position P3 above the cap-closing position P1.

Specifically, the arm bracket 42 is first moved in the X direction and Y direction, and the opening/closing arm 41 is moved to a position where the cap 13 is clamped, which corresponds to a feed position P2 on the feed table 45 that exists on a lateral side of the cap-closing position P1. Then, the opening/closing arm 41 is closed to grasp the cap 13 that is set on the feed table 45. Further, the opening/closing arm 41 in the state in which it grasps the cap 13 is moved in the X direction and retreated from the feed table 45, and then the opening/closing arm 41 is moved to the cap-closing position P1 in the Y direction. Thereby, the cap 13 is disposed at the predetermined standby position P3 which is located below the holding shaft 26 and above the specimen container 11.

If the specimen container 11, which is held by the holder 12, stops at the cap-closing position P1, the control device 40 drives the moving motor 36 and rotating motor 31, and moves downward and rotates the holding shaft 26.

By the rotation of the moving motor 36, the pinion gear 38 rotates, and thereby the rack gear 37, which is meshed with the pinion gear 38, moves downward together with the support frame 23. In addition, the support shaft 26, which is supported by the support frame 23, moves downward. At this time, the holding shaft 26 is inserted in the holding hole 13d of the cap 13 that is disposed below the holding shaft 26. Furthermore, by the lowering of the holding shaft 26, the cap 13 is pushed and lowered.

The cap 13, which was pushed and lowered by the holding shaft 26, is displaced downward from the opening/closing arm 41, and is put on the upper part of the specimen container 11 that is disposed below. At this time, the upper opening edge of the specimen container 11 is inserted in the insertion portion 13a of the cap 13.

Following the above, by the rotation of the rotating motor 31, the holding shaft 26 rotates in a predetermined direction. In the meantime, since the insertion portion 27a has the tapered shape with a gradually decreasing thickness, the insertion portion 27a is so guided as to be inserted in the space between the longitudinal plates 13e when the holding shaft 26 moves downward and rotates, even if the longitudinal plates 13e of the cap 13 and the slit 27b are misaligned. Then, by the slit 27b of the holding shaft 26 being engaged with the longitudinal plates 13e of the holding hole 13d of the cap 13, the relative rotation between the cap 13 and holding shaft 26 is restricted, and the cap 13 rotates together with the holding shaft 26. By this rotation, the male screw portion 1ie of the specimen container 11 is engaged with the female screw portion 13b of the cap 13, and thus the cap 13 is closed successively.

At this time, the torque acting on the holding shaft 26 is detected by the torque sensor 35 and sent to the control device 40. The control device 40 detects the torque, and controls the rotating motor 31 to stop the rotation at a time point when the detected value has reached a preset predetermined value.

By the above, the cap 13 is attached to the upper opening 11b of the specimen container 11 by a desired fastening force, and the cap-closing process is completed. If the cap-closing process is completed, the holding shaft 26 is raised, and the opening/closing arm 41 of the feeding mechanism section 25 is opened and moved to the feed table 45. By repeating the above procedure at a predetermined timing, the cap-closing process is successively performed for attaching the caps 13, which are successively fed to the standby position P3 from the feed table 45, to the specimen containers 11 which are successively fed to the cap-closing position P1. The specimen container 11 after the cap closing is further conveyed to the downstream side by the operation of the convey unit 10.

According to the cap-closing section 20 and the cap-closing method relating to the present embodiment, the following advantageous effects can be obtained. Specifically, by detecting the torque which is caused by the rotation of the cap 13, and by controlling the amount of rotation in accordance with this torque, the screw-type cap 13 can be attached with a proper fastening force. Therefore, a high sealing performance can be secured.

In addition, the cap-closing process is completed by such a simple operation that the holding shaft 26 is lowered and rotated in the state in which the cap 13 is made to stand by between the specimen container 11 and holding shaft 26. Therefore, the cap-closing process for many specimen containers 11 can be performed exactly in a short time.

Furthermore, the holding process and attaching process can be performed by providing, on the cap 13 side, the holding hole and the longitudinal plates 13e which can transmit a driving force in the rotational direction. In addition, since each insertion portion 27a is formed in the tapered shape with a gradually decreasing thickness, the insertion portion 27a is so guided as to be inserted in the space between the longitudinal plates 13e when the holding shaft 26 moves downward and rotates, even if the longitudinal plates 13e of the cap 13 and the slit 27b are misaligned. Therefore, since the cap 11 is configured to have a simple structure which is easy to form and includes a plurality of longitudinal plates 13e extending in the radial direction and axial direction, the manufacturing cost can be reduced. Moreover, even without executing such control as strict alignment in the rotational direction with respect to the cap 13 and holding shaft 26, the cap 13 can exactly be screwed, by the holding shaft 26, on the specimen container 11 which is conveyed along the convey path.

The present invention is not limited to the above-described embodiments. In practice, various modifications may be made without departing from the spirit of the invention. Further, various inventions may be made by suitably combining a plurality of components described in connection with the foregoing embodiment. For example, some of the components according to the foregoing embodiment may be omitted. Furthermore, components according to different embodiments may be combined as required.

What is claimed is:

1. A cap-closing apparatus comprising:
a holding mechanism section configured to be capable of holding a cap which is attached to an opening of a specimen container that is formed to be capable of containing a specimen;
a moving mechanism section configured to move the cap;
a rotating mechanism section configured to rotate the cap;
a torque detector configured to detect a torque at a time of rotation; and
a controller configured to control an amount of rotation of the rotating mechanism section, based on the torque detected by the torque detector,
wherein the holding mechanism section comprises a holding shaft comprising an engaging section configured to be engageable with the cap,
a screw portion is provided on an opening edge of the specimen container,
an inner peripheral surface of an insertion section, which is formed on one end side in an axial direction of the cap, is provided with a screw portion configured to be engaged with the screw portion of the specimen container,
a holding hole, in which the holding shaft of the holding mechanism section is inserted, is formed on the other end side in the axial direction of the cap, and a plurality of longitudinal plates extending in a radial direction are provided in a circumferential direction in an inside of the holding hole, and the engaging section comprises a plurality of slits provided at a distal end of the holding shaft and configured such that the longitudinal plates are insertable in the slits, and a plurality of insertion portions having a tapered shape and provided between a plurality of the slits, the slits and the insertion portions being arranged alternately in the circumferential direction.

2. The cap-closing apparatus of claim 1, further comprising a feeding mechanism section configured to feed the cap to a position between the specimen container and the holding shaft at a cap-closing position, wherein the moving mechanism section is configured to move the holding shaft toward the specimen container, thereby holding and moving the cap disposed between the holding shaft and the specimen container, and attaching the cap to the opening of the specimen container, and the cap is engaged with the screw portion of the specimen container by rotating the holding shaft.

3. The cap-closing apparatus of claim 1, wherein the holding mechanism section comprises a holding shaft comprising an engaging section configured to be engaged with the cap, the rotating mechanism section comprises a motor configured to rotate the holding shaft, and the moving mechanism section comprises a rack gear provided on a support section configured to support the rotating mechanism section and the holding mechanism section, and a pinion gear which is rotatable and is configured to be engageable with the rack gear.

4. A cap-closing unit comprising:

the cap-closing apparatus of claim 1; and a convey unit configured to convey, along a predetermined path, a holder configured to be capable of holding the specimen container in an upright state.

5. A cap-closing method comprising:

in a state where a cap is arranged above an opening of a specimen container including an opening edge on which a screw portion is provided, the cap including a screw portion provided on an inner peripheral surface of an insertion section, which is formed on one end side in an axial direction of the cap, a holding hole formed on the other end side in the axial direction of the cap, and a plurality of longitudinal plates extending in the axial direction and a radial direction and provided in a circumferential direction in an inside of the holding hole, moving a holding shaft including a plurality of slits to be engaged with the longitudinal plates and a plurality of insertion portions having a tapered shape and provided between a plurality of the slits, the slits and the insertion portions being arranged alternately in a circumferential direction, toward the specimen container while inserting the holding shaft into the holding hole of the cap so that the longitudinal plates are engaged with the slits;

screwing the cap on the specimen container by rotating the holding shaft;

detecting a torque acting on the holding shaft at a time of the rotating; and controlling a rotating operation of the holding shaft, based on the detected torque.

6. A cap-closing apparatus comprising:

a holding mechanism section comprising a rotatable holding shaft configured to be engageable with a cap which is attached to an opening of a specimen container that is formed to be capable of containing a specimen;

a torque detector configured to detect a torque at a time of rotation of the holding shaft; and a controller configured to control an amount of rotation of the holding shaft, based on the torque detected by the torque detector, wherein the holding shaft comprises an engaging section configured to be engageable with the cap, a screw portion is provided on an opening edge of the specimen container, an inner peripheral surface of an insertion section, which is formed on one end side in an axial direction of the cap, is provided with a screw portion configured to be engaged with the screw portion of the specimen container, a holding hole, in which the holding shaft of the holding mechanism section is inserted, is formed on the other end side in the axial direction of the cap, and a plurality of longitudinal plates extending in a radial direction are provided in a circumferential direction in an inside of the holding hole, and the engaging section comprises a plurality of slits provided at a distal end of the holding shaft and configured such that the longitudinal plates are insertable in the slits, and a plurality of insertion portions having a tapered shape and provided between a plurality of the slits, the slits and the insertion portions being arranged alternately in the circumferential direction.

* * * * *